US012728077B2

(12) United States Patent
Fu et al.

(10) Patent No.: US 12,728,077 B2

(45) Date of Patent: Sep. 8, 2026

(54) TOOTH MINERALIZATION SOLUTION AND MINERALIZATION METHOD THEREOF

(71) Applicant: ZHEJIANG UNIVERSITY, Hangzhou City (CN)

(72) Inventors: Baiping Fu, Hangzhou City (CN); Zihuai Zhou, Hangzhou City (CN); Zhifang Wu, Hangzhou City (CN)

(73) Assignee: ZHEJIANG UNIVERSITY, Hangzhou City (CN)

( * ) Notice: Subject to any disclaimer, the term of this patent is extended or adjusted under 35 U.S.C. 154(b) by 1295 days.

(21) Appl. No.: 17/504,447

(22) Filed: Oct. 18, 2021

(65) Prior Publication Data

US 2022/0031575 A1 Feb. 3, 2022

Related U.S. Application Data

(63) Continuation of application No. PCT/CN2020/086568, filed on Apr. 24, 2020.

(30) Foreign Application Priority Data

Nov. 5, 2019 (CN) ........................ 201911071426.5

(51) Int. Cl.

*A61K 6/20* (2020.01)
*A61K 6/838* (2020.01)
*A61K 6/891* (2020.01)

(52) U.S. Cl.

CPC ................ *A61K 6/20* (2020.01); *A61K 6/838* (2020.01); *A61K 6/891* (2020.01)

(58) Field of Classification Search

CPC .......... A61K 6/20; A61K 6/838; A61K 6/891; A61K 6/831

See application file for complete search history.

(56) References Cited

FOREIGN PATENT DOCUMENTS

| | | | | |
|---|---|---|---|---|
| CN | 1187117 | A | | 7/1998 |
| CN | 1192672 | A | | 9/1998 |
| CN | 105267046 | A | * | 1/2016 |
| CN | 106473933 | A | | 3/2017 |

OTHER PUBLICATIONS

CN-105267046-A Trnaslation (Year: 2016).*

"John2001—A trial to prepare biodegradable collagen-hydroxyapatite composites for bone repair" (Jun. 15, 2001) [A John et al.].

* cited by examiner

*Primary Examiner* — Snigdha Maewall

(74) *Attorney, Agent, or Firm* — Wiersch Law Group

(57) ABSTRACT

Disclosure is a tooth mineralization solution and a mineralization method thereof. The tooth mineralization solution can be used to mineralize collagen and teeth. The mineralization solution component of the present application comprises two parts, namely, reagent A containing non-collagenous protein analogue and calcium salt, and reagent B is phosphate solution. The mineralization method of the tooth mineralization solution of the present application comprises the steps of first applying the reagent A to the surface of tooth, and then applying the reagent B to achieve tooth mineralization. In addition, the mineralization solution of the present application can also be used to achieve biomimetic mineralization of collagen by the same method, comprising the steps of soaking or floating single-layer reconstituted collagen fibril, collagen gel or collagen sponge in the reagent A, and then soaking or floating in the reagent B to achieve biomimetic mineralization.

6 Claims, 5 Drawing Sheets

TOOTH MINERALIZATION SOLUTION AND MINERALIZATION METHOD THEREOF

TECHNICAL FIELD

The present application belongs to the field of biological materials and, in particularly, relates to a tooth mineralization solution and a method for applying to teeth and collagen mineralization.

BACKGROUND

As we all know, the tooth structurally includes an inner dentin layer and an enamel shell. Dentin is composed of mineralized collagens orderly arranged in a multi-level way. Hydroxyapatite crystals are deposited on the surface of the collagen template and the inner interstitial area in an orderly manner. The minerals in these fibrils are particularly important for the mechanical properties and biological properties of teeth and bones. However, the complexity of the structure makes dentin mineralization a difficult point in biomimetic mineralization. There are also dentin tubules in the dentin, which communicate with the dental pulp. If acid etching, abrasion, or gingival recession and other factors cause the loss of enamel or cementum and the demineralization of dentin, it will lead to exposure of the dentin tubules, and thus hot and cold stimulation or mechanical stimulation will cause the dentin hypersensitivity.

The methods that have been used for tooth mineralization or dentin tubule occlusion includes fluoride, bioactive glass, Green Or desensitizer, adhesive and so on. However, the effects of mineralization of teeth and occlusion of dentin tubules are unstable.

The current mainstream dentin remineralization model is that the demineralized dentin is immersed in the non-collagenous proteins (NCPs) analogue-stabilized amorphous calcium phosphate (ACP) mineralization solution. After ACP from mineralization solution enters the collagen, it is converted into hydroxyapatite to achieve intrafibrillar mineralization. Because calcium and phosphate ions in saturation solution of ACP are very low, calcium and phosphate ions are very slowly replenished. This leads to the time-consuming procedure of biomineralization and its results are plausible. Bioactive glass can also be used for the mineralization of teeth, but it has a nature of transience and instantly releases a large amount of calcium and phosphate ions without stabilization of NCPs or their analogues, and the clinical efficacy of tooth mineralization is not good as expected in lab. The existing tooth mineralization products, such as mouthwash and toothpaste, are in contact with teeth for a short time and cannot provide a sufficient source of calcium and phosphate ions.

Patent CN105267046 also proposes a method for rapidly mineralizing dentin, in which through the synthesis of NCPs analogue-stabilized amorphous calcium phosphate solution, the demineralized dentin is soaked in a mineralization solution for 2 days to achieve mineralization. Because it is affected by the solubility and saturation of calcium phosphate, as the concentrations of calcium and phosphate ions increase, the calcium phosphate salt precipitation will be generated rapidly. In the existing amorphous calcium phosphate mineralization solution used for mineralization, the calcium ion usually does not exceed 50 mmol, so the rate of supplying calcium and phosphate for mineralization is still relatively slow.

Moreover, the prepared calcium-phosphate mixed mineralization solutions or amorphous calcium phosphates are prone to phase transition and then precipitate as hydroxyapatite crystals, which cannot be stored to maintain their bioactivity for a long time even though they are stabilized by NCPs or their analogues.

The object of at least one aspect of the present application is to solve or eliminate at least one or more of the aforementioned problems.

The object of at least one aspect of the present application is to provide a tooth mineralization solution which can be stored for a long time.

The object of at least one aspect of the present application is to provide a method for applying the tooth mineralization solution to teeth and collagen mineralization.

SUMMARY

The object of the present application is to provide a tooth mineralization solution and a method for applying the tooth mineralization solution to teeth and collagen mineralization in order to overcome the defects of long treatment time, unstable mineralization effect, continuous supply of calcium and phosphate sources, and difficulty of long-term storage of mineralization solution in teeth and collagen mineralization technology.

The present application provides a tooth mineralization solution, comprising a reagent A and a reagent B;

the reagent A contains NCPs analogue and calcium salt; the NCPs analogue is one or more of a group consisting of polyelectrolytes such as polyaspartic acid, polyacrylic acid, polyvinylphosphonic acid, polyglutamic acid, carboxymethyl chitosan, sodium trimetaphosphate and sodium tripolyphosphate; its average molecular weight is about 300-100000. Preferably, the average molecular weight of the NCPs analogue is about 300-40000. The calcium salt is one or more of a group consisting of calcium chloride or a hydrate thereof, calcium fluoride or a hydrate thereof, calcium carbonate or a hydrate thereof, calcium nitrate or a hydrate thereof, or calcium acetate or a hydrate thereof.

The reagent B is a phosphate solution; the phosphate is one or more of a group consisting of trisodium phosphate, tripotassium phosphate, disodium hydrogen phosphate, dipotassium hydrogen phosphate, sodium dihydrogen phosphate, potassium dihydrogen phosphate, triammonium phosphate, ammonium dihydrogen phosphate and diammonium hydrogen phosphate; preferably, potassium phosphate is used, which can also provide potassium ions, and more effectively realize the depolarization of the nerves that are exposed within the dentinal tubules.

In the tooth mineralization solution, an appropriate amount of fluoride, such as one of sodium fluoride, potassium fluoride, calcium fluoride, zinc fluoride, stannous fluoride, zinc ammonium fluoride, laurylamine hydrofluoride, and diethylaminoethyl octanamide hydrofluoride or a combination thereof, can also be added to the reagent A or reagent B to increase the anti-caries performance of the material, and the addition amount is 0.1%-10% by mass fraction of the tooth mineralization solution.

In the tooth mineralization solution, an appropriate amount of a sweetener, such as one of saccharin, cyclohexane sulfamate, sucrose, glucose and potassium acesulfame or a combination thereof, can also be added, and the addition amount is 0.1%-10% by mass fraction of the tooth mineralization solution.

In the tooth mineralization solution, an appropriate amount of a humectant, such as one of polyethylene glycol (a variety of different molecular weights), propylene glycol, glycerol (glycerin), erythritol, xylitol, sorbitol, mannitol and lactitol or any mixture thereof, can be added, and the addition amount is 0.1%-10% by mass fraction of the tooth mineralization solution.

In the tooth mineralization solution, an appropriate amount of an antibacterial agent, such as one of benzoic acid, sodium benzoate, potassium benzoate, boric acid, phenolic compounds such as β naphthol, chlorothymol, thymol, anethole, cineole, carvacrol, menthol, phenol, amylphenol, hexylphenol, heptylphenol, octylphenol, hexylresorcinol, laurylpyridinium chloride, myristylpyridinium chloride, cetylpyridinium fluoride, cetylpyridinium chloride, and cetylpyridinium bromide or any mixture thereof, can also be added to increase the antibacterial and bactericidal properties of the material, and the addition amount is 0.1-10% by mass fraction of the tooth mineralization solution.

In the tooth mineralization solution, an appropriate amount of a collagen cross-linking agent, such as one of 1-(3-dimethylaminopropyl)-3-ethylcarbodiimide hydrochloride and other carbodiimides, D-ribose, and cyclodextrin polyaldehydes or any mixture thereof, can also be added to help stabilize the collagen fiber network, and the addition amount is 0.1%-5% by mass fraction of the tooth mineralization solution.

The dosage volume ratio of the reagent A to the reagent B is (1:0.1)-10, and the molar ratio of the concentration of calcium ions in the reagent A to the total concentration of phosphates, monohydrogen phosphate and dihydrogen phosphate in the reagent B is (1-10):1; the reagent A and the reagent B are stored separately.

In the reagent A, the content of NCPs analogue is 0.001 g/L-20 g/L, and the concentration of calcium ions is 0.2 mol/L-10 mol/L.

In the reagent B, the total concentration of phosphate radical, monohydrogen phosphate radical and dihydrogen phosphate radical in the phosphate solution is 0.2 mol/L-10 mol/L.

As a preferred solution of the present application, in the reagent A, the content of non-collagen analogue is 5 g/L-10 g/L, and the concentration of calcium ions is 5.2 mol/L-10 mol/L; in the reagent B, the total concentration of phosphate radical, monohydrogen phosphate radical and dihydrogen phosphate radical in the phosphate solution is 5 mol/L-10 mol/L.

The solution A of the tooth mineralization solution system of the present application must first react with collagen, and in the presence of a small amount of polyelectrolyte, polyelectrolyte-calcium complexes are formed, which quickly transports numerous calcium ions into the collagen first, and then attracts phosphate ions into the collagen. It is different from the use of synthetic amorphous calcium phosphate, because at high concentrations, a large amount of NCPs analogue needs to be added to stabilize the amorphous calcium phosphate. According to the published patent document (CN1488574), its highest calcium concentration is 5M, and it is mixed with the phosphate solution to prepare ACP. Therefore, its actual final calcium concentration is lower than 5M, and its effect of mineralizing collagen fibers is unstable. It is essentially different from the present application, which uses a biomimetic mineralization model of calcium first and then phosphate guided by a polyelectrolyte-calcium complex. The existing mineralization model is to use NCPs analogue-stabilized amorphous calcium phosphate as a mineralization precursor to induce biomimetic mineralization.

As a preferred embodiment of the present application, the NCPs analogue includes sodium trimetaphosphate and sodium tripolyphosphate. Usually in the field of mineralization, the object of using small molecular oligomers such as sodium trimetaphosphate and sodium tripolyphosphate is to first modify the collagen by phosphorylation, and then mineralize the modified collagen with a polymer-stabilized amorphous calcium phosphate solution. These oligomers are currently not used to stabilize amorphous calcium phosphate. In the present application, a complex is formed by small molecular oligomers and calcium, and a good mineralization effect can be obtained without adding other polyelectrolytes.

The present application also discloses a method for preparing the tooth mineralization solution, which comprises the following steps:

Dissolving the calcium salt and the NCPs analogue in deionized water and adjusting the pH value to 5-12 to obtain reagent A; and dissolving phosphate in deionized water and adjusting the pH value to 5-12 to obtain reagent B.

The present application also discloses a tooth mineralization method of the tooth mineralization solution, which comprises the following steps:

1) First applying the reagent A to the tooth surface for 3 s-30 min, then allowing the reagent A to stand for 1 min-60 min; and then applying the reagent B to the tooth surface for 3 s-30 min and allowing the reagent B to stand for 1 min-60 min;
2) Repeating step 1) several times or not repeating step 1), and then placing the teeth in artificial saliva or deionized water for 1 day to achieve the mineralization of teeth, where in the pH of artificial saliva or deionized water is 5-9.

More preferably, the surface applying time of the two reagents is about 5 min-10 min, and the standing time of the two reagents is about 3 min-5 min. The dentin tubules can be quickly sealed by the treatment of the tooth mineralization solution, and the hydroxyapatite formed can reach the dentin tubules at a depth of 200 μm-300 μm. After standing in artificial saliva for about 1 day, the intrafibrillar mineralization of full-thickness demineralized dentin can also be obtained.

The present application also discloses a collagen mineralization method of the tooth mineralization solution: 1) soaking or floating the single-layer reconstituted collagen fibril, the collagen gel or the collagen sponge in the reagent A for 3 s-30 min, and then taking out and blotting dry with filter paper, and then soaking or floating in the reagent B for 3 s-30 min; 2) repeating step 1) several times or not repeating step 1); then placing the collagen in artificial saliva or deionized water at a temperature of 37° C. and allowing it to stand for 1 min-24 h to achieve biomimetic mineralization and generate a mineralized collagen. That is, after collagen fibrils are treated with the reagent A of the tooth mineralization solution, it can be mixed with the reagent B to generate mineralized collagen material. As the main organic component of dentin, type I collagen can also be mineralized with the tooth mineralization solution. Among them, artificial saliva is used to simulate the environment in the oral cavity, and even if it is placed in deionized water, the collagen can still be mineralized.

The present application also discloses use of the tooth mineralization solution in the preparation of dental care products, and the dental care products include: drugs used for dentin tubule occlusion and tooth desensitization, drugs used to prevent or treat dental erosion, and oral care products for dental care and periodontal scaling.

The mineralized hydrogel is obtained by mixing the reagent A, the reagent B, a gelling agent, and deionized water. The mineralized hydrogel can be used for 3D printing to prepare bone powder, bone cement or dental restorations. According to needs, a curing agent, a foaming agent and polyelectrolytes can also be added during the mixing process of mineralized hydrogel; the gelling agent is selected from one of methyl cellulose, sodium alginate, sodium carboxymethyl cellulose, carboxypropyl methyl cellulose, hydroxypropyl methyl cellulose, chitosan, polypropylene glutarate, and polycaprolactone.

Compared with the prior art, the present application has the following beneficial effects:

The tooth mineralization solution of the present application is different from the original low-concentration calcium phosphate mineralization solution. By increasing the concentration and separating calcium from phosphate, the penetration of the tooth mineralization solution in the dentin tubules and collagen fibrils can be enhanced. By adding the NCPs analogue such as polyaspartic acid to the reagent A of the tooth mineralization solution, calcium ions are stabilized, and the rate of formation of hydroxyapatite crystals when contacted with phosphate ions is slowed down, which is conducive to the penetration of the reagent B to reach the deep dentin tubules. In addition, under high concentration conditions, a large amount of hydroxyapatite crystals can be generated, which tightly occlude the dentin tubules, is close to the hydroxyapatite component in natural dentin, and has better bio-compatibility. It overcomes the shortcomings that the sealing depth is shallow, it is easy to fall off and wear, the preparation cost is high, and it needs to be used repeatedly for a long time in the prior art. It effectively isolates the external stimulation to the dentin tubules, is conducive to long-term storage, and has a broad market prospect. In addition, the rapid treatment of tooth mineralization solution can quickly provide a large amount of calcium and phosphorus ions for demineralized dentin collagen, which can be used as a mineral source for dentin collagen mineralization, the full-thickness mineralization can be achieved by standing in artificial saliva that simulates the oral environment for about 1 day, and the existing problems of long mineralization time of demineralized dentin, unstable mineralization effect, and continuous supply of calcium and phosphorus sources are also solved.

The tooth mineralization solution of the present application will be extremely useful. It can not only be used in the oral cavity, but also can be treated for a few minutes to achieve the collagen intrafibrillar mineralization within 1 day. The synthetic raw materials used do not contain toxic materials and the biological safety is good, and it also has the prospect of synthesizing bone graft related materials.

BRIEF DESCRIPTION OF DRAWINGS

wherein FIG. 2*a* is the surface morphology of the dentin sample after treatment with the tooth mineralization solution; FIG. 2*b* is the longitudinal section morphology of the dentin sample after treatment with the tooth mineralization solution; FIG. 2*c* is an enlarged view of the dentin tubules close to the surface in FIG. 2*b*.

wherein FIG. 3*a* indicates the TEM image of reconstituted type I collagen at 5000-folds after mineralization treatment in Example 1; FIG. 3*b* indicates the TEM image of reconstituted type I collagen at 10,000-folds after mineralization treatment in Example 1; FIG. 3*c* indicates is an SAED pattern of reconstituted type I collagen after mineralization treatment in Example 1b.

DESCRIPTION OF EMBODIMENTS

The present application will be further explained and illustrated below in conjunction with the accompanying drawings and specific embodiments. The technical features of the various embodiments of the present application can be combined accordingly without conflict with each other.

Example 1

30 g of calcium chloride and 3 g of polyaspartic acid were dissolved in 20 ml of water and the pH was adjusted to 7 for preparing a reagent A. A reagent B was prepared according to the ratio of calcium to phosphorus of 1.67, and the pH was adjusted to 7.

Preparation of demineralized dentin discs: a dentin disc with a size of about 3*3*2 mm was prepared, etched with 37% phosphoric acid for 15 s, and rinsed with deionized water for 30 s. The reagent A was applied to the surface of the dentin for 20 min and left undisturbed for 10 min. Then the reagent B was applied for 20 min and left undisturbed for 10 min.

Preparation of a single-layer reconstituted type I collagen model: 8 μL of rat tail type I collagen fibril stock solution was taken and dissolved in 0.5 mL of buffer solution (50 mM glycine, 200 mM potassium chloride, pH=9.2); 3 μL of a collagen solution was pipetted onto a Nickel TEM grid, placed in a 37° C. thermotank for more than 10 hours, retrieved and then cross-linked with 0.05 wt % of glutaraldehyde for 1 hour, and the excess glutaraldehyde solution was rinsed for later use.

Figure 1A:
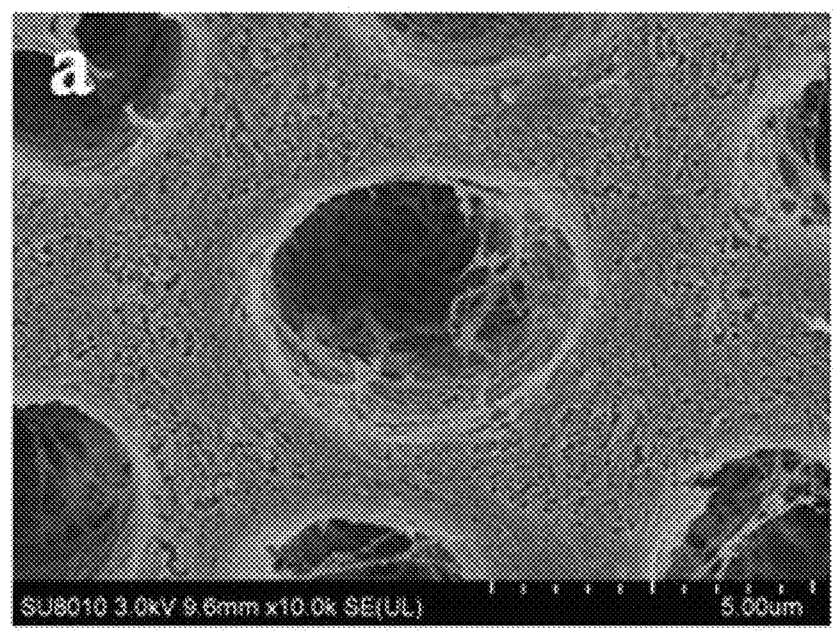
FIG. 1*a* is a scanning electron microscope (SEM) image of the surface of demineralized dentin.
Figure 1B:
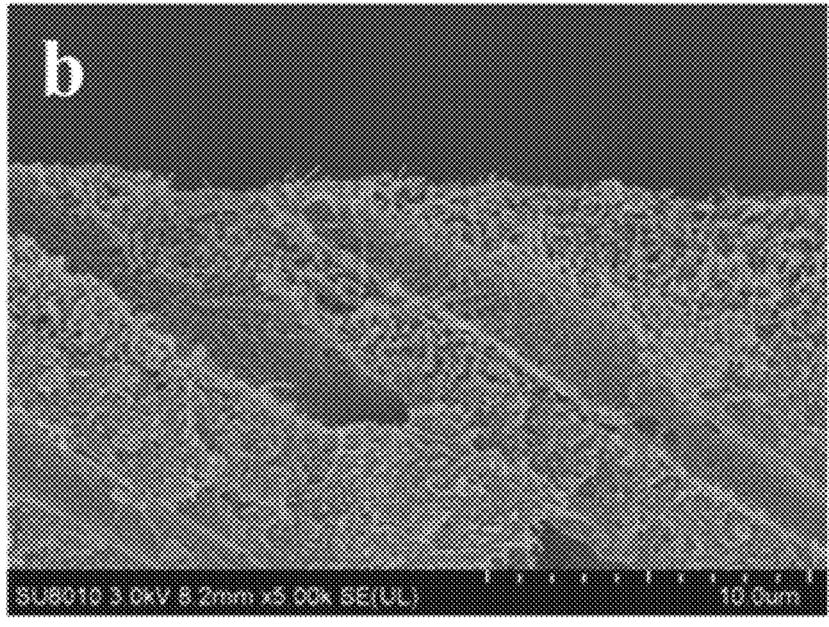
FIG. 1*b* is a scanning electron microscope (SEM) image of the longitudinal section of dentin tubules after demineralization.

Mineralization of single-layer reconstituted collagen: the collagen-loaded grid was floated on the reagent A for 10 minutes, and retrieved, then the excess reagent A was blotted up, and then the grid was floated on the reagent B for treating for 10 minutes, and then retrieved and dried; then the grid was placed on artificial saliva that was prepared in advance at a pH of 6-8 at a temperature of 37° C. for 1 hour; after the grid was dehydrated with deionized water, a 50% alcohol aqueous solution, and anhydrous alcohol in turn, it was observed with TEM and SAED FIG. 1 is an SEM image of a demineralized dentin sample, FIG. 1*a* is the surface morphology of dentin after demineralization, and FIG. 1*b* is the longitudinal section morphology of dentin tubules after demineralization. The above-mentioned images prove that demineralization can completely expose the dentin tubules, and there are no minerals in the dentin tubules.

Figure 2:
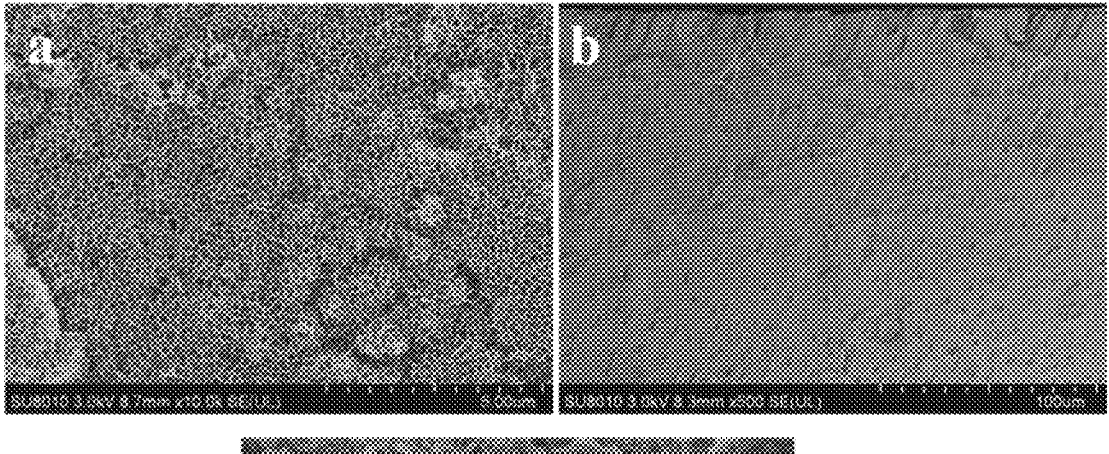
FIG. 2 is an SEM image of a dentin sample after treatment with a tooth mineralization solution in Example 1.
Figure 2:
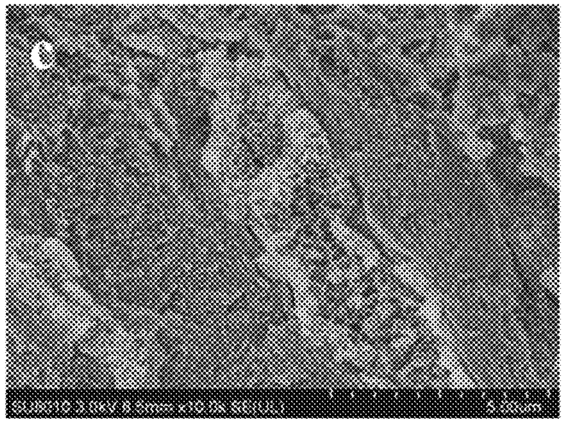

FIG. 2 is an SEM image of a demineralized dentin sample treated with a tooth mineralization solution, wherein FIG. 2*a* shows that after the surface of demineralized dentin is treated with the tooth mineralization solution of the present application, the surfaces of the dentin tubules can be covered with a dense and uniform layer of hydroxyapatite; FIG. 2*b* shows that the depth to which the tooth mineralization solution can penetrate into the dentin tubules is about 200 μm; FIG. 2*c* is an enlarged view of the dentin tubules in FIG. 2*b*, showing that the dentin tubule lumen is tightly occluded by hydroxyapatite, wherein the atomic percentage of the elements (Ca/P) of minerals filled in the dentin tubules is 1.69.

Figure 3:
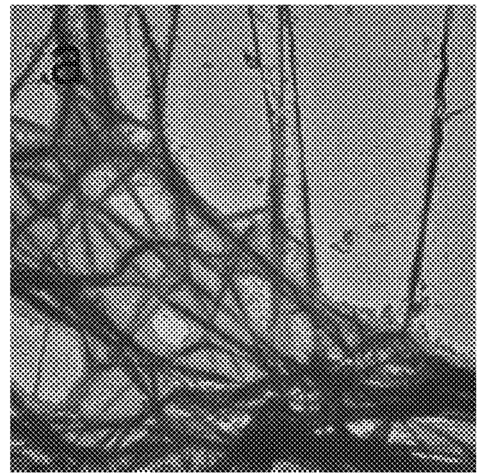
FIG. 3 is a TEM image of reconstituted type I collagen after mineralization treatment in Example 1.
Figure 3:
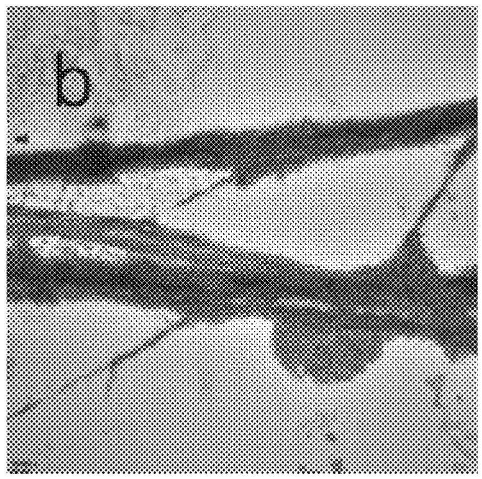
Figure 3:
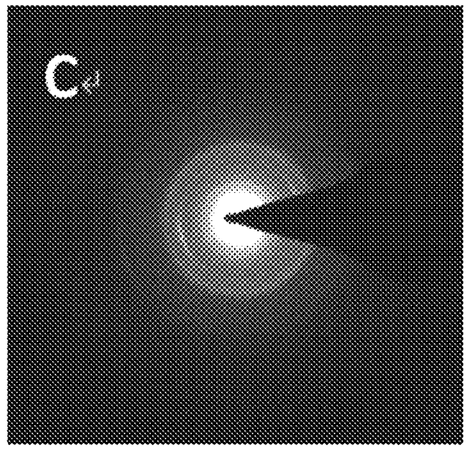

FIG. 3 is a TEM image of single-layer reconstituted type I collagen. It is found that obvious mineralization occurs inside and outside the collagen fibril (FIG. 3*a*, FIG. 3*b*). The SAED result (FIG. 3*c*) shows that the crystals inside and outside the collagen are hydroxyapatite.

The above-mentioned embodiment is only a preferred solution of the present application, but it is not intended to limit the present application. Those of ordinary skill in the relevant technical field can make various changes and modifications without departing from the spirit and scope of the present application. Therefore, all technical solutions obtained by equivalent substitutions or equivalent transformations fall within the protection scope of the present application.

Example 2

10 g of calcium chloride and 10 g of polyaspartic acid were dissolved in 20 ml of water, and the pH was adjusted to 8 for preparing a reagent A. A reagent B was prepared according to the ratio of calcium to phosphorus of 1.67, and the pH was adjusted to 8.

Preparation of demineralized dentin discs: a dentin disc with a size of about 3*3*2 mm was prepared, etched with 37% phosphoric acid for 15 s, and rinsed with deionized water for 30 s.

Mineralization of demineralized dentin discs: the reagent A was applied to the surface of the dentin for 15 min and left undisturbed for 5 min. Then the reagent B was applied for 15 min and left undisturbed for 5 min. Then, the treated dentin discs was put in artificial saliva with a pH of 7 that was prepared in advance at a temperature 37° C. and left undisturbed for 24 hours. After the tooth discs were dehydrated with an ascending series of 50-100% alcohol-aqueous solution, they were fixed with acetone and embedding resin, sectioned and then observed with TEM.

Figure 4:
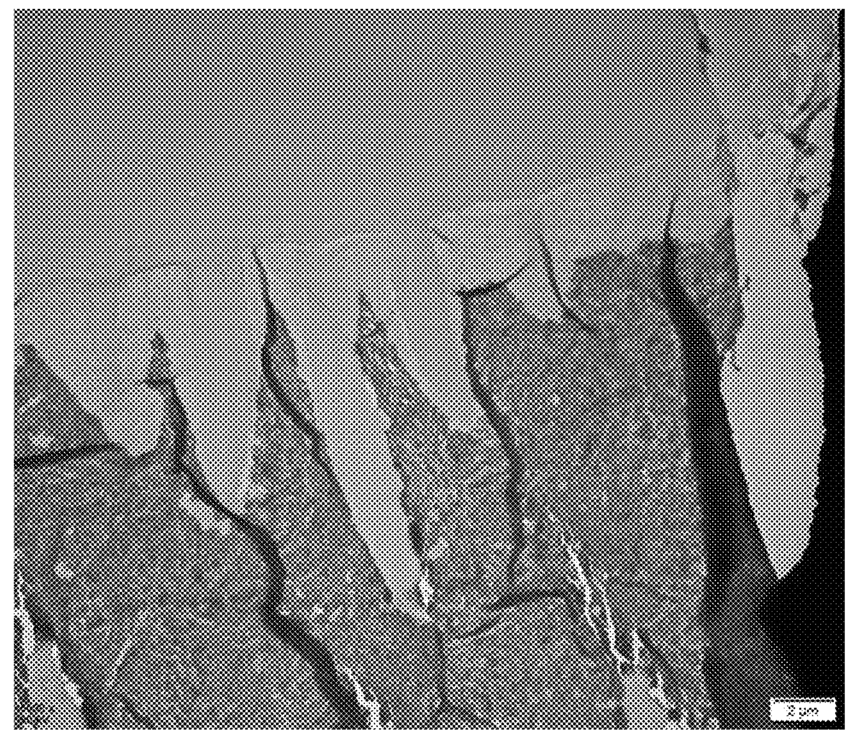
FIG. 4 is a TEM image of the demineralized dentin sample in Example 2.

FIG. 4 is a TEM image of a demineralized dentin sample. The above-mentioned image reveals that the demineralization layer of dentin is about 2-4 μm thick after demineralization, and the minerals in the collagen of the demineralized layer cannot be detected, which becomes a transparent collagen network.

Figure 5:
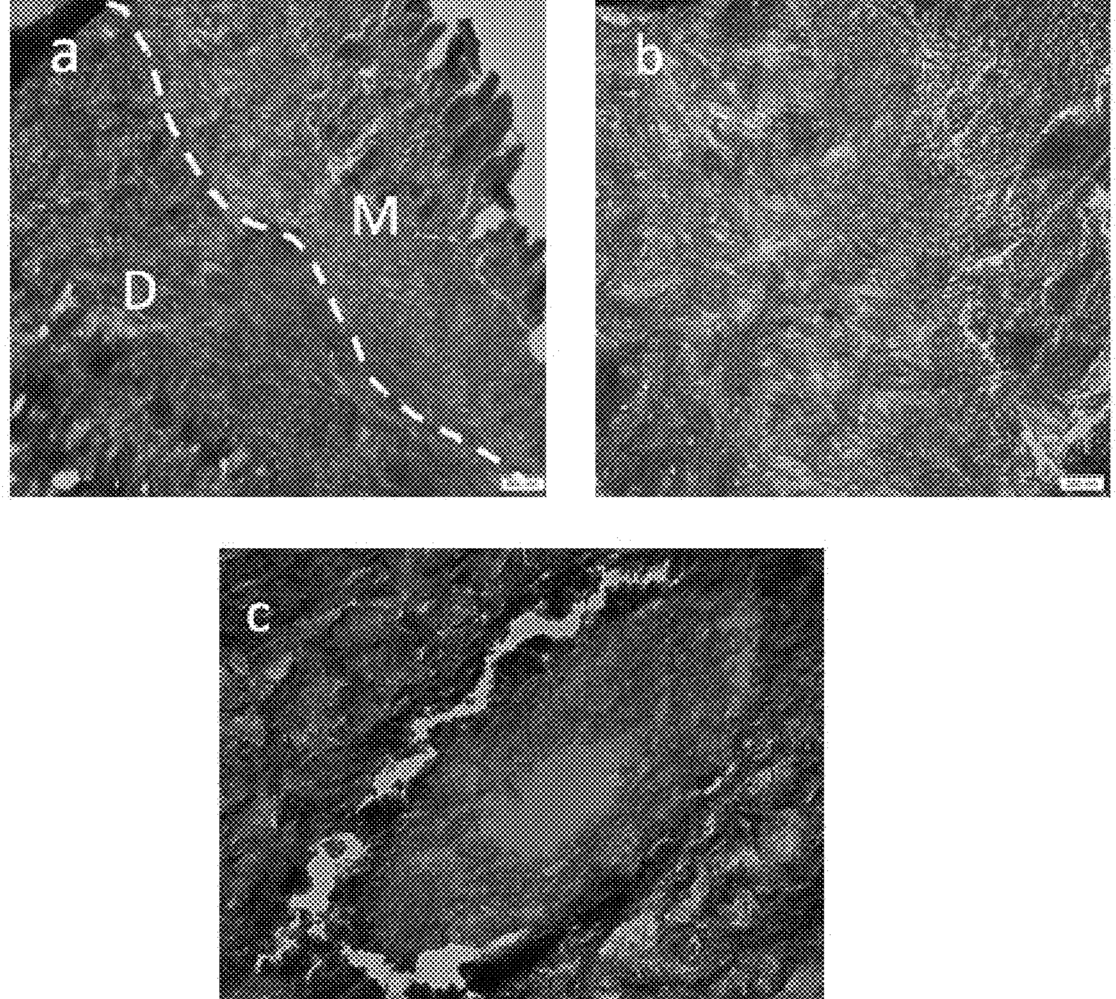
FIG. 5 is a TEM image of the demineralized dentin sample after treatment with the tooth mineralization solution in Example 2.

FIG. 5 is a TEM image of a demineralized dentin sample after treatment with a tooth mineralization solution, wherein FIG. 5*a* shows that after the surface of the demineralized dentin is treated with the tooth mineralization solution of the present application, and the demineralized layer is remineralized (region M), the structure is similar to that of the intact dentin (region D); FIG. 5*b* is a magnificated image of FIG. 5*a*, showing that the collagen remineralization of the demineralization layer is intrafibrillar mineralization, and the crystal orientation is parallel to the long axis of the collagen fiber; FIG. 5*c* is an enlarged view of dentin tubules at a depth of 100 μm under the demineralization layer, showing that the dentin tubule lumen is filled and occluded by hydroxyapatite.

The above-mentioned embodiment is only a preferred solution of the present application, but it is not intended to limit the present application. Those of ordinary skill in the relevant technical field can make various changes and modifications without departing from the scope of the present application. Therefore, all technical solutions obtained by equivalent substitutions or equivalent transformations fall within the protection scope of the present application.

What is claimed is:

1. A tooth mineralization solution, comprising a reagent A and a reagent B;

wherein the reagent A is a solution comprising non-collagenous protein analogue and calcium salt; the non-collagenous protein analogue is one or more of a group consisting of polyaspartic acid, polyacrylic acid, polyvinylphosphonic acid, polyglutamic acid, carboxymethyl chitosan, sodium trimetaphosphate or sodium tripolyphosphate; the calcium salt is one or more of a group consisting of calcium chloride or a hydrate thereof, calcium fluoride or a hydrate thereof, calcium carbonate or a hydrate thereof, calcium nitrate or a hydrate thereof, or calcium acetate or a hydrate thereof; in the reagent A, the non-collagenous protein analogue accounts for 0.001 g/L-20 g/L, and a concentration of calcium ions is 0.001 mol/L-10 mol/L;

the reagent B is a phosphate solution; the phosphate is one or more of a group consisting of trisodium phosphate, tripotassium phosphate, disodium hydrogen phosphate, dipotassium hydrogen phosphate, sodium dihydrogen phosphate, potassium dihydrogen phosphate, triammonium phosphate, ammonium dihydrogen phosphate or diammonium hydrogen phosphate; in the reagent B, a total concentration of phosphate radical, monohydrogen phosphate radical and dihydrogen phosphate radical in the phosphate solution is 0.001 mol/L-10 mol/L;

the dosage volume ratio of the reagent A to the reagent B is 1:(0.1-10), and the molar ratio of the concentration of calcium ions in the reagent A to the total concentration of phosphate, monohydrogen phosphate and dihydrogen phosphate in the reagent B is (0.1-10):1; and the reagent A and the reagent B are stored separately.

2. The tooth mineralization solution according to claim 1, wherein in the reagent A, the non-collagenous protein analogue accounts for 3 g/L-10 g/L, and the concentration of calcium ions is 5.2 mol/L-10 mol/L; in the reagent B, the total concentration of phosphate, monohydrogen phosphate and dihydrogen phosphate in the phosphate solution is 5 mol/L-10 mol/L.

3. The tooth mineralization solution according to claim 1, wherein the non-collagenous protein analogue comprises polyaspartic acid, polyacrylic acid, polyvinylphosphonic acid, sodium trimetaphosphate or sodium tripolyphosphate.

4. A method for preparing the tooth mineralization solution according to claim 1, comprising:

dissolving the calcium salt and the non-collagenous protein analogue in deionized water and adjusting the pH value to 5-12 to obtain the reagent A; and dissolving phosphate in deionized water and adjusting the pH value to 5-12 to obtain the reagent B.

5. A method for preparing a mineralized collagen from the tooth mineralization solution according to claim 1, comprising:

1) Soaking or floating single-layer reconstituted collagen fibril, collagen gel or collagen sponge in the reagent A for 3 s-30 min, and then taking out and blotting up with filter paper, and then soaking or floating in the reagent B for 3 s-30 min;

2) Repeating step 1) several times or not repeating step 1); then placing the collagen in artificial saliva or deionized water at a temperature of 37° C. and allowing the collagen to stand for 1 min-24 h to achieve biomimetic mineralization and generate the mineralized collagen.

6. Dental care products preparing by the tooth mineralization solution according to claim 1, wherein the dental care products comprise oral care products for mineralization of teeth, prevention of dental erosion, dental care and periodontal care.

* * * * *